(12) United States Patent
Meijering et al.

(10) Patent No.: US 7,601,137 B2
(45) Date of Patent: Oct. 13, 2009

(54) NEEDLE-LESS INJECTOR

(75) Inventors: Antonie Hendrikus Meijering, Reuver (NL); Andreas Johannes Maria Jacobs, 's-Hertogenbosch (NL)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 10/515,801

(22) PCT Filed: Jun. 5, 2003

(86) PCT No.: PCT/EP03/05963

§ 371 (c)(1),
(2), (4) Date: Mar. 31, 2006

(87) PCT Pub. No.: WO03/103751

PCT Pub. Date: Dec. 18, 2003

(65) Prior Publication Data

US 2006/0217661 A1    Sep. 28, 2006

(30) Foreign Application Priority Data

Jun. 10, 2002    (EP)    ................................. 02077263

(51) Int. Cl.
*A61M 5/30*    (2006.01)
(52) U.S. Cl. ........................................................ 604/68
(58) Field of Classification Search ............. 604/68–72, 604/134, 218–231
See application file for complete search history.

(56) References Cited

U.S. PATENT DOCUMENTS

| | | | | |
|---|---|---|---|---|
| 3,129,708 | A * | 4/1964 | Krantz ........................ | 604/68 |
| 3,859,996 | A * | 1/1975 | Mizzy et al. ................. | 604/70 |
| 4,002,996 | A | 1/1977 | Klebanoff et al. | |
| 5,480,381 | A * | 1/1996 | Weston ........................ | 604/68 |
| 5,542,920 | A * | 8/1996 | Cherif Cheikh ............. | 604/57 |
| 5,851,198 | A * | 12/1998 | Castellano et al. ........... | 604/68 |
| 5,891,086 | A * | 4/1999 | Weston ........................ | 604/70 |
| 6,425,879 | B1 * | 7/2002 | Egger et al. .................. | 604/68 |
| 7,207,967 | B1 * | 4/2007 | Bellhouse et al. ............ | 604/70 |
| 2006/0217661 | A1 * | 9/2006 | Meijering et al. ........... | 604/134 |

FOREIGN PATENT DOCUMENTS

EP    0 346 548    12/1989

(Continued)

*Primary Examiner*—Kevin C Sirmons
*Assistant Examiner*—Michael J Anderson
(74) *Attorney, Agent, or Firm*—William M. Blackstone

(57) ABSTRACT

The invention relates to a needle-less injector having a housing comprising: a chamber defined within said injector for containing liquid to be injected; a liquid outlet for said chamber positioned at the front end of the injector, a dispensing member in contact with the liquid in said chamber and movable in a first direction to reduce the volume of said chamber to cause the liquid contained therein to be expelled through said liquid outlet; drive means for actuating said injector, wherein the dispensing member is a spring-loaded piston movable in said chamber by the spring in the first direction to a preferred position at which the volume of said chamber is at a minimum and the spring is nearly unloaded, and which piston is movable in a second direction opposite to the first direction by actuation of the drive means whilst counteracting a force from the spring and moving the piston to a non-preferred position at which the spring is loaded.

12 Claims, 3 Drawing Sheets

FOREIGN PATENT DOCUMENTS

| | | |
|---|---|---|
| FR | 1 518 915 A | 3/1968 |
| FR | 2639544 A1 * | 6/1990 |
| FR | 2641190 A1 * | 7/1990 |
| JP | 07100204 | 4/1995 |
| WO | WO 98 13085 | 4/1998 |
| WO | WO 9813085 A1 * | 4/1998 |
| WO | WO 03103751 A1 * | 12/2003 |

* cited by examiner

NEEDLE-LESS INJECTOR

PRIORITY CLAIM TO RELATED PATENT APPLICATIONS

This patent claims priority under 35 U.S.C. §371 to International Patent Application No. PCT/EP2003/05963 (filed Jun. 5, 2003), which, in turn, claims priority to EP Patent Application No. 02077263.8 (filed Jun. 10, 2002). The entire text of each of the above-referenced patent applications is incorporated by reference into this patent.

FIELD OF THE INVENTION

Embodiments of the present invention generally relate to needless injectors.

BACKGROUND OF THE INVENTION

The invention relates to a needle-less injector having a housing comprising:
- a chamber defined within said injector for containing liquid to be injected;
- a liquid outlet for said chamber positioned at the front end of the injector;
- a dispensing member in contact with the liquid in said chamber and movable in a first direction to reduce the volume of said chamber to cause the liquid contained therein to be expelled through said liquid outlet;
- drive means for actuating said injector.

Such a needle-less injector is known from WO 98/13085.

The known needle-less injector has a housing that is essentially unitary and is further characterized in that it utilises an impacting member arranged to strike said dispensing member to cause movement thereof in said first direction and that the drive means are connected to the impacting member for actuating the injector.

A problem with this known needle-less injector is that in order to secure continued operation for a prolonged time-span the construction of the known needle-less injector should be heavy. A further disadvantage is that the utilization of the impacting member to strike the dispensing member to cause its movement is very inefficient in terms of utilization of the available energy.

The invention aims in improving the known needle-less injector and addressing the above-mentioned problems.

SUMMARY OF THE INVENTION

The needle-less injector according to the invention is to that end characterized in that the dispensing member is a spring-loaded piston movable in said chamber by the spring in the first direction to a preferred position at which the volume of said chamber is at a minimum and the spring is nearly unloaded, and which piston is movable in a second direction opposite to the first direction by actuation of the drive means whilst counteracting a force from the spring and moving the piston to a non-preferred position at which the spring is loaded.

The beauty of the needle-less injector according to the invention is that a separate impacting member to cause movement of the dispensing member is avoided. The problems that are associated with the use of a separate impacting member that are explained above are therewith completely solved.

DETAILED DESCRIPTION OF THE INVENTION

A particularly suitable construction of the needle-less injector according to the invention is characterized in that the piston is fixed to a movable member having a cam follower positioned on said member, and that the drive means is connected to a rotatable cam having a highest point and a lowermost point immediately following said highest point, which cam co-operates with said cam follower, so as to cause that rotation of the cam is converted into longitudinal movement of the member and the piston that is fixed to said member.

In the known needle-less injector the liquid outlet of the chamber is equipped with a non-return valve, whereby the chamber has a liquid inlet which is arranged to allow liquid to enter into the chamber when the piston is moved to the non-preferred position, i.e. the position in which the chamber has its largest volume.

In a further aspect of the invention at least part of the liquid inlet of the chamber is formed by the front end of the piston. This construction offers some advantages which shall become apparent from the further discussion below.

In a further aspect of the invention at least part of the liquid inlet of the chamber is formed by a central bore extending through at least part of the piston, which central bore has an outlet to the chamber. This construction offers some further advantages which shall become apparent from the further discussion below.

It is particularly advantageous that near the non-preferred position of the piston the central bore is in open fluid communication with a supply-line for the fluid.

The benefits of the just-mentioned construction are completely attained when the supply-line has an outlet adjacent to which sealing organs are provided, that co-operate with the piston and that the piston is provided with at least one essentially radial channel that extends to the bore within the piston and which channel has an opening at the piston's circumference that is in open fluid communication with the outlet of the supply line only when the piston is near the non-preferred position.

Entirely depending on the position that the piston assumes with respect to the opening of the supply-line, the chamber then can be filled with liquid to be used for injecting purposes. Whilst retracting the piston from the preferred position to the non-preferred position the liquid outlet of the chamber is closed by the action of the non-return valve. Consequently the retraction of the piston causes under-pressure in the chamber. At the moment the piston assumes or is near the non-preferred position the liquid for injecting purposes flows from the outlet of the supply-line through the piston's radial channel and bore to the chamber under the influence of the under-pressure that is present in said chamber.

Another advantage that attaches to the just-mentioned construction is the following. When the piston is in the non-preferred position and the needle-less injector is ready for operation so as to cause the liquid to be expelled through the injector's liquid outlet, the piston can initially be accelerated in order to reduce the volume of the chamber in which the liquid is contained, which acceleration can occur without much loss or friction. The access amount of liquid in the chamber which would otherwise restrict the acceleration of the piston can initially leave the chamber through the piston's central bore and radial channel by means of it's open fluid communication with the supply line for the fluid. This can continue up to the moment that the piston has left the non-preferred position to such extend that the open fluid communication of the piston's radial channel with the outlet of the supply-line is lost.

Effectively the sealing organs are O-rings, and the piston is moveable through said O-rings.

In still another aspect of the invention the supply-line is provided with a sensor for detecting the presence of liquid for injecting purposes, whilst the operation of the drive means is dependent on the sensor.

This allows that the drive means are enabled to reciprocate without the cam follower passing the cam's highest point to cause moving the piston back- and forward when the sensor fails to detect liquid for injecting purposes. The said moving the piston back- and forward causes a pumping action suitable for feeding liquid for injecting purposes to the chamber whilst the aspect that the cam follower does not pass the cam's highest point prevents that the piston drives out such liquid through the liquid outlet of the chamber.

Accordingly it is further desirable that the drive means are enabled to cause the cam follower to pass the cam's highest point when the sensor detects liquid for injecting purposes.

The sensor can e.g. be a combination of a light emitting diode (LED) and a light-sensitive detector opposite the LED, placed over the supply-line 17. The supply-line 17 is preferably made of a transparent material such as Teflon. If no liquid or a colourless cleaning liquid such as water is present in the supply-line, the light of the LED will be detected by the light-sensitive sensor. If however a liquid for injection purposes passes the sensor, less or no light of the LED will be detected by the sensor. This is due to the fact that liquid for injection purposes is by nature practically always opaque.

BRIEF DESCRIPTION OF THE FIGURES

The invention shall hereafter be further elucidated with reference to the drawings of a non-limiting preferred embodiment of the injector according to the invention. In the drawings.

Same reference numerals used in the drawings refer to identical or similar parts.

Figure 1:
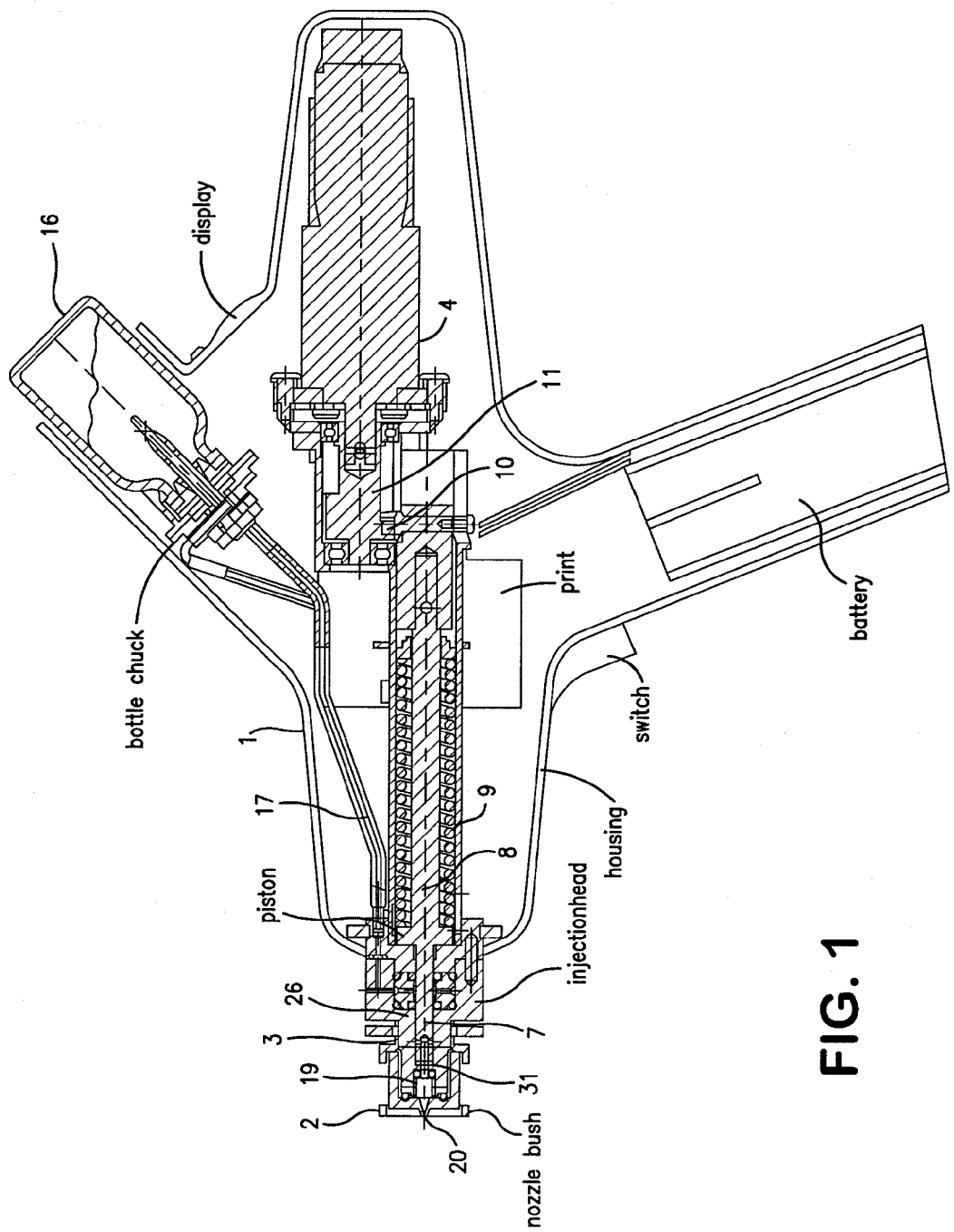
FIG. 1 shows a sectional view of the injector according to the invention with the piston in the preferred position.

With reference first to FIG. 1 the injector comprises a single housing denoted with reference numeral 1 at the front edge of which a moveable front portion 2 is attached which can be moved in the direction of arrow A when placed against the epidermis of a human, animal or plant.

A spring 3 urges the front portion 2 to assume a position distant from the unitary housing 1. This position is shown in the drawing of FIG. 1. Behind the front end portion 2 a cylinder 26 is provided in which the piston 7 can move in its longitudinal direction. The piston 7 borders at its front area a chamber 31 in the cylinder 26 for the liquid to be used for injecting purposes. This chamber 31 is clearly shown in FIG. 3 wherein the piston 7 is near its non-preferred position. In FIG. 1 and in the corresponding figure 2 the chamber 31 is at its minimum volume.

The cylinder 26 is provided with a non-return valve 18 at the side of the front end portion 2. The cylinder 26 is connected through a tube or supply-line 17 to a reservoir 16 containing the liquid that is to be injected. The reservoir is equipped with means to permit air to enter the bottle as the liquid is dispensed therefrom. A discharge nozzle 20 is sealingly connected to the chamber 31 within the cylinder 26 and a non-return valve 19 biased to its closed position by a compression spring prevents air being drawn into the cylinder 26 whilst the piston 7 is moving from the preferred position shown in FIGS. 1 and 2 to the non-preferred position shown in FIG. 3.

The piston 7 is fixed to a moveable member 8 which is spring-loaded by means of spring 9 urging the member 8 and the piston 7 that is connected thereto to a preferred position at which the volume of chamber 31 is at minimum.

Movement of the moveable member 8 and the piston 7 connected thereto in the direction A, so as to cause that the volume of chamber 31 is increased, is caused by actuating of a motor 4 which is housed in the rear end of the housing 1. The output shaft of the motor 4 carries a cylindrical cam 11 to which is engaged a cam follower 10 which is attached to the moveable member 8. The motor is preferably of the electric type, but it is within the ambit of the invention to apply another type of motor, for example gas-powered.

Figure 2:
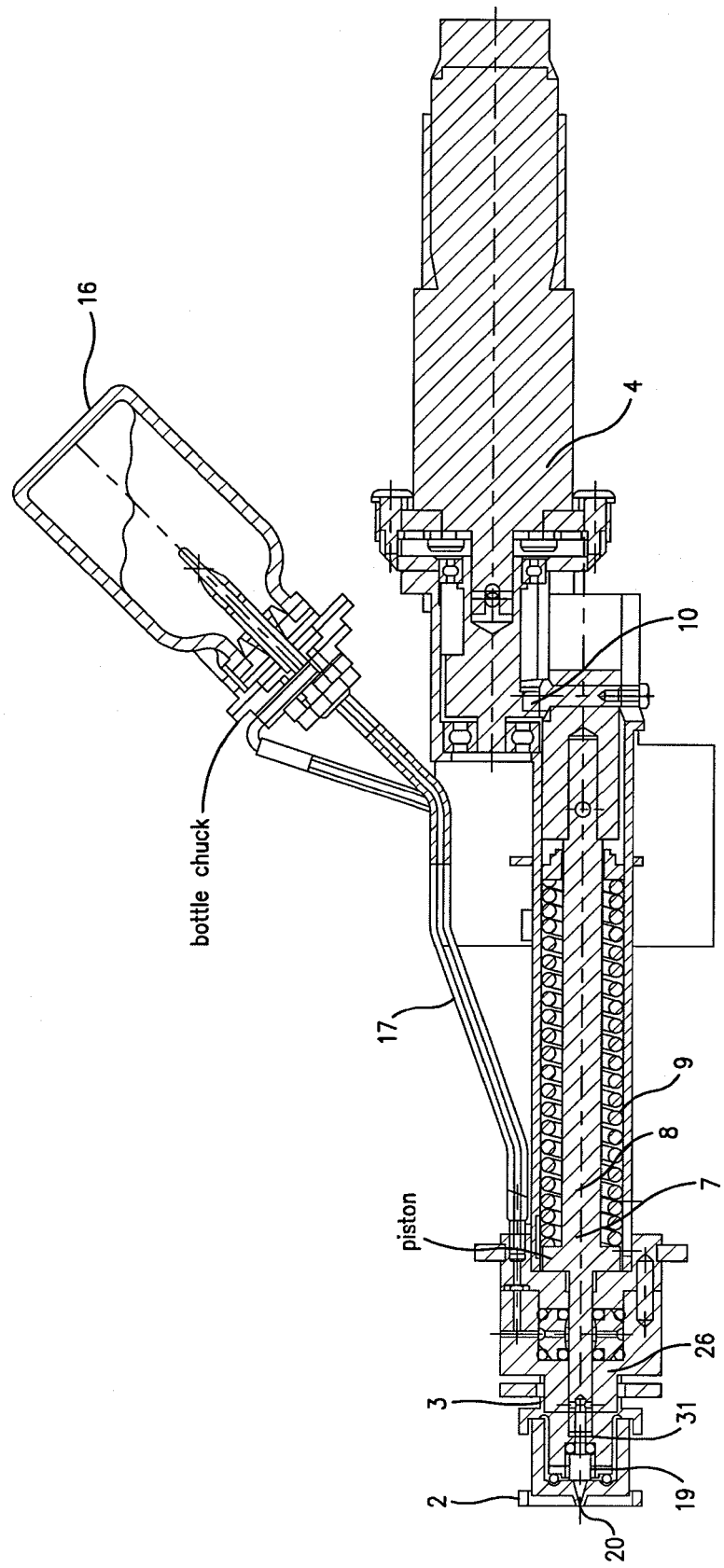
FIG. 2 shows the apparatus of FIG. 1 without the housing.
Figure 3:
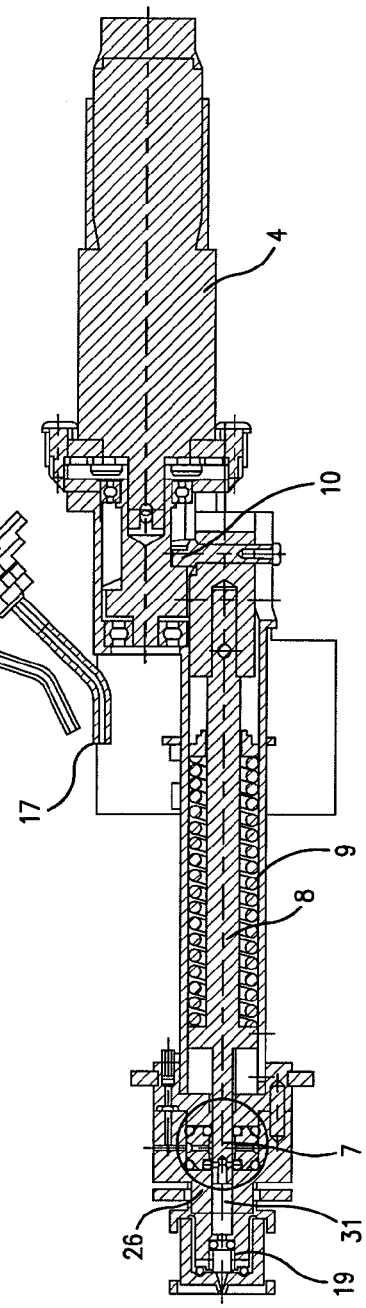
FIG. 3 shows the apparatus of FIG. 1 without the housing whilst the piston is placed in the non-preferred position.
Figure 5:
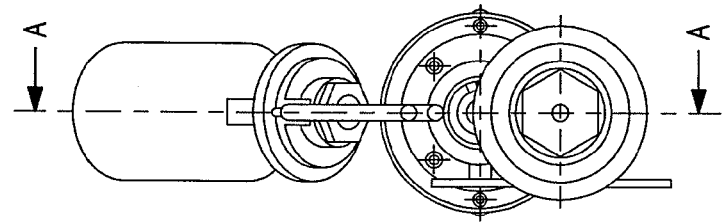
FIG. 5 shows the front view of the apparatus shown in FIG. 3.

FIG. 3 shows the situation in which the cam follower 10 is located near the end of the ramp provided by the cam 11 and the volume of chamber 31 is near its maximum due to the fact that in this position the piston 7 is largely removed from the area of this chamber 31. FIGS. 1 and 2 show the piston 7 largely filling the area of the chamber 31 whereby the cam follower 10 is located at the beginning of the ramp provided by the cam 11. Evidently rotation of the cam 11 converts into longitudinal movement of the moveably member 8 and the piston 7 that is connected thereto.

Figure 4:
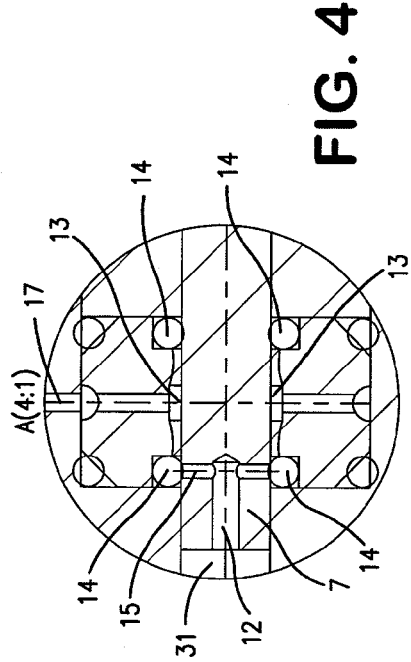
FIG. 4 shows a detail of the apparatus shown in FIG. 3.

When moving the piston 7 to its non-preferred position as shown in FIG. 3 and the detail of piston 7 in figure 4, the volume of chamber 31 increases whilst non-return valve 19 closes off the chambers 31 outlet. Consequently, in chamber 31 an increasing under-pressure builds up. The chamber 31 is provided with a liquid inlet which is arranged to allow liquid to enter into the chamber when the piston 7 is moved to the non-preferred position (see FIGS. 3 and 4). This liquid inlet includes a central bore 12, extending through at least part of the piston 7, which bore has an outlet for liquid to enter the chamber 31.

The supply-line 17 for feeding liquid from the reservoir 16 to the chamber 31 has an outlet 13 next to which sealing organs 14 are provided that co-operate with the piston 7. The piston 7 is further provided with one or more radial channels 15, extending to the bore 12 within the piston 7. These channels 15 are arranged that they show an opening at the piston's 7 circumference that is in open fluid communication with the outlet 13 of the supply-line 17 only when the piston 7 is near the non-preferred position. FIG. 4 shows the situation that the piston 7 approaches this non-preferred position. The drawing further shows the preferred embodiment in which the sealing organs 14 are O-rings and that the piston 7 is moveable through these O-rings 14.

The operation of the needle-less injector according to the invention may be identical to the manner of operation of the needle-less injector according to the prior art. For instance this operation may be dependent on the front end portion being placed under pressure against the epidermis of an animal. A clear description of this operation is available to the man skilled in the art from the publication WO 98/13085, the content of which is incorporated herein by reference.

A further feature that differentiates the needle-less injector according to the invention from the known injector is that the supply-line 17 is provided with a sensor (not shown) for detecting the presence of liquid for injecting purposes whereby the operation of the motor 4 is dependent on said sensor.

Particularly, the motor 4 is enabled to reciprocate without the cam follower 10 passing the cam's 11 highest point to cause moving the piston 7 back- and forward when the said sensor fails to detect liquid for injecting purposes. This continued back- and forward moving of the piston 7 causes a pumping action for the liquid to suck into the chamber 31 and until said liquid reaches the sensor, this pumping action is continued. Accordingly, the motor is enabled to cause the cam follower 10 to pass the cam's 11 highest point when the sensor detects liquid for injecting purposes. When that happens the spring 9 urges the moveable member 8 and the piston 7 connected thereto to progressively diminish the volume of chamber 31. Initially the piston 7 then accelerates quickly due to the access amount of liquid in the chamber 31 being able to leave said chamber through the central bore 12, the radial channel 15 connected thereto and from there through the outlet 13 back into the supply line 17. With the continued motion of the piston 7 the radial channel 15 moves past the left O-ring 14 and closes off the open fluid communication between the central bore 12 and the outlet 13 of the supply line 17 resulting eventually in expelling the liquid contained in the chamber 31 whilst passing the non-return valve 19 in order to effectuate an injection with that liquid. Thereafter the motor 4 may retract the piston 7 from its preferred position arrived at when the volume of chamber 31 is at its minimum as shown in FIGS. 1 and 2, to return same to the position shown in FIGS. 3 (and 4) in order to repeat the injecting operation.

We claim:

1. A needle-less injector having a housing, wherein the injector comprises:
    a chamber for containing liquid to be injected;
    a supply line for transferring liquid from a reservoir to the chamber;
    a liquid outlet for the chamber positioned at the front end of the injector;
    a single piece dispensing member in contact with the liquid in the chamber and movable in a first direction to reduce the volume of the chamber to cause the liquid contained in the chamber to be expelled through the liquid outlet;
    a drive means for actuating the injector, wherein the dispensing member is a single piece piston with a spring attached thereto, whereby the single piece piston is spring-loaded and is:
        movable in the chamber by the spring in the first direction to a preferred position at which the volume of the chamber is at a minimum and the spring is nearly unloaded, and
        movable in a second direction opposite to the first direction by actuation of the drive means whilst counteracting a force from the spring and moving the piston to a non-preferred position at which the spring is loaded and
    a sensor associated with the supply line that detects the presence or absence of liquid to be injected in the supply line, said sensor being linked to the drive means, whereby the dispensing member is not actuated by the drive means when the absence of liquid to be injected is detected in the supply line.

2. A needle-less injector according to claim 1, wherein:
    the piston is fixed to a movable member having a cam follower positioned on the member,
    the drive means is connected to a rotatable cam having a highest point and a lowermost point immediately following the highest point, and
    the cam co-operates with the cam follower so that rotation of the cam is converted into longitudinal movement of the member and the piston that is fixed to the member.

3. A needle-less injector according to claim 2, wherein:
    the liquid outlet of the chamber is equipped with a non-return valve,
    the chamber has a liquid inlet which is arranged to allow liquid to enter into the chamber when the piston is moved to the non-preferred position,
    at least part of the liquid inlet of the chamber is formed by a central bore extending through at least part of the piston, and
    the central bore has an outlet to the chamber.

4. A needle-less injector according to claim 3, wherein the central bore is in open fluid communication with the supply-line for the liquid to be injected when the piston is near the non-preferred position.

5. A needle-less injector according to claim 4, wherein:
    the supply-line has an outlet adjacent to which sealing organs are provided,
    the sealing organs co-operate with the piston,
    the piston is provided with at least one essentially radial channel that extends to the bore within the piston, and
    the channel has an opening at the piston's circumference that is in open fluid communication with the outlet of the supply line only when the piston is near the non-preferred position.

6. A needle-less injector according to claim 5, wherein:
    the sealing organs are O-rings, and
    the piston is moveable through the O-rings.

7. A needle-less injector according to claim 1, wherein the drive means are enabled to reciprocate without the cam follower passing the cam's highest point to cause moving the piston back and forward when the sensor fails to detect liquid to be injected.

8. A needle-less injector according to claim 1, wherein the drive means are enabled to cause the cam follower to pass the cam's highest point when the sensor detects liquid to be injected.

9. A needle-less injector according to claim 1, wherein:
    the liquid outlet of the chamber is equipped with a non-return valve,
    the chamber has a liquid inlet which is arranged to allow liquid to enter into the chamber when the piston is moved to the non-preferred position,
    at least part of the liquid inlet of the chamber is formed by a central bore extending through at least part of the piston, and
    the central bore has an outlet to the chamber.

10. A needle-less injector according to claim 9, wherein the central bore is in open fluid communication with a supply-line for the fluid when the piston is near the non-preferred position.

11. A needle-less injector according to claim 10, wherein:
    the supply-line has an outlet adjacent to which sealing organs are provided,
    the sealing organs co-operate with the piston,
    the piston is provided with at least one essentially radial channel that extends to the bore within the piston, and
    the channel has an opening at the piston's circumference that is in open fluid communication with the outlet of the supply line only when the piston is near the non-preferred position.

12. A needle-less injector according to claim 11, wherein:
    the sealing organs are O-rings, and
    the piston is moveable through the O-rings.

* * * * *